United States Patent [19]

Beutler

[11] Patent Number: 5,401,724
[45] Date of Patent: Mar. 28, 1995

[54] THERAPEUTIC TREATMENT OF CHRONIC MYELOGENOUS LEUKEMIA BY ADMINISTRATION OF 2-CHLORO-2'-DEOXY ADENOSINE

[75] Inventor: Ernest Beutler, La Jolla, Calif.

[73] Assignee: The Scripps Research Institute, La Jolla, Calif.

[21] Appl. No.: 202,672

[22] Filed: Feb. 25, 1994

Related U.S. Application Data

[63] Continuation of Ser. No. 61,179, May 13, 1993, abandoned, which is a continuation-in-part of Ser. No. 885,348, May 19, 1992, abandoned.

[51] Int. Cl.$^6$ ............................................ A61K 31/70
[52] U.S. Cl. .................................. 514/46; 536/27.63; 536/27.7
[58] Field of Search ............... 514/46; 536/27.4, 27.63, 536/27.8

[56] References Cited

U.S. PATENT DOCUMENTS

| | | | |
|---|---|---|---|
| 4,751,221 | 6/1988 | Watanabe et al. | 514/46 |
| 4,918,179 | 4/1990 | Watanabe et al. | 536/27.4 |
| 5,034,518 | 7/1991 | Montgomery et al. | 536/27.4 |
| 5,106,837 | 4/1992 | Carson et al. | 514/46 |
| 5,310,732 | 5/1994 | Carson | 514/46 |

OTHER PUBLICATIONS

Carson et al.(I), "Antileukemic and Immunosuppressive Activity of 2-Chloro-2'-deoxyadenosine," *Proc. Nat. Acad. Sci. USA*, 81, 2232–2236 (1984).

Platanias et al., "Hairy Cell Leukaemia: The Role of Alpha Interferon," *Eur. J. Cancer*, 27(Supp. 4), S53–S57 (1991).

Petzer et al., "Inhibitory Effect of 2-Chlorodeoxyadenosine on Granulocytic, Erythroid, and T-Lymphocytic Colony Growth," *Blood*, 78(10), 2583–2587 (1991).

Jehn et al., "New Drugs in the Treatment of Acute and Chronic Leukemia with Some Emphasis on m-AMSA," *Anticancer Research*, 11, 705–712 (1991).

Carson et al.(II), "Programmed Cell Death and Adenine Deoxynucleotide Metabolism in Human Lymphocytes," *Adv. Enzyme Regul.*, 27, 395–404 (1988); *MEDLINE*, Abstr. No. 89269905; Only Abstract provided.

Scholtz, "New Drugs and Other Treatments in the Management of Cancer," *Am. J. Pharm.*, 164, 15–22 (1992).

*Textbook of Medicine, Cecil*. 18th Ed., Wyngaarden et al. eds., W. B. Saunders Co., 1992, Philadelphia, Pa., pp. 933–949.

Reiter et al., "A Dual Anti-Tumor Effect of a Combination of Interferon-α and 5-Fluorouracil or 2-Chlorodeoxyadenosine on Natural Killer (NK) Cell Mediated Cytotoxicity," in *Purine and Pyrimidine Metabolism in Man, Part A*, Harkness et al. eds., Plenum Press, New York, 1991, pp. 69–73.

Ho, "Chemotherapy of Chronic Haematological Malignancies," *Balliere's Clin. Haematology*, 4(1), 197–221 (1991).

Piro et al., "2-Chlorodeoxyadenosine: An Effective New Agent for the Treatment of Chronic Lymphocytic Leukemia," *Blood*, 72(3), 1069–1073 (1988).

Beutler et al., "2-Chlorodeoxyadenosine (2-CdA): A Potent Chemotherapeutic and Immunosuppressive Nucleoside," *Leukemia and Lymphoma*, 5, 1–8 (1991).

Gandhi et al., "Cell Cycle-Specific Metabolism of Arabinosyl Nucleosides in K562 Human Leukemia Cells," *Cancer Chemother. Pharmacol.*, 31, 11–17 (1992).

Klein, *IMMUNOLOGY The Science of Self-Nonself Discrimination*, John Wiley & Sons, New York, 1982, pp. 92–94 and 98–101.

Saven et al., "Complete Hematologic Remissions in Chronic-Phase, Philadelphia Chromosome-Positive, Chronic Myelogenous Leukemia after 2-Chlorodeoxyadenosine," *Cancer*, 73(12), 2953–2963 (1994).

*Primary Examiner*—John W. Rollins
*Assistant Examiner*—L. Eric Crane
*Attorney, Agent, or Firm*—Welsh & Katz, Ltd.

[57] ABSTRACT

A process for the treatment of chronic myelogenous leukemia in mammals is disclosed that utilizes a 2-halo-2'-deoxyadenosine derivative as the active treating agent.

8 Claims, No Drawings

THERAPEUTIC TREATMENT OF CHRONIC MYELOGENOUS LEUKEMIA BY ADMINISTRATION OF 2-CHLORO-2'-DEOXY ADENOSINE

This invention was made with government support under Contract No. RR 00833 awarded by the National Institutes of Health. The government has certain rights in the invention.

CROSS-REFERENCE TO RELATED APPLICATION

This application is a continuation of application Ser. No. 08/061,179, filed May 13, 1993, now abandoned, which is a continuation-in-part of application Ser. No. 07/885,348, filed May 19, 1992, now abandoned, whose disclosures are incorporated by reference.

TECHNICAL FIELD

This invention relates to a novel treatment for chronic myelogenous leukemia. More particularly, this invention relates to a process for the treatment of chronic myelogenous leukemia involving the administration of a 2-halo-2'-deoxyadenosine.

BACKGROUND OF THE INVENTION

An adult human has about 7000 white blood cells per microliter ($\mu$l) of blood. Of those white cells, about 65 percent are granulocytes (about 4500/$\mu$l), about 30 percent are monocytes (about 2100/$\mu$l) and about five percent are lymphocytes (about 350/$\mu$l). Geyton, *Textbook of Medical Physiology*, Seventh ed., W. B. Saunders Co., Philadelphia (1986). The above cell numbers are, of course, generalized average values, and granulocyte counts for normal patients; i.e., patients that do not have DML or a similar disease exhibiting an increased or decreased granulocyte count, typically have granulocyte counts ranging from about 2000 to about 7000 cells/$\mu$l.

Chronic myelogenous leukemia (CML), also known as chronic granulocytic leukemia (CGL), is a neoplastic disorder of the hematopoietic stem cell. In its early phases it is characterized by leukocytosis, the presence of increased numbers of immature granulocytes in the peripheral blood, splenomegaly and anemia. These immature granulocytes include basophils, eosinophils, and neutrophils. The immature granulocytes also accumulate in the bone marrow, spleen, liver, and occasionally in other tissues. Patients presenting with this disease characteristically have more than 75,000 white blood cells per microliter ($\mu$l), and the count may exceed 500,000/$\mu$l.

CML accounts for about 20 percent of all leukemias in the United States. About 15 new cases per million people are reported each year, leading to about 3,000 to 4,000 new cases per year. The disease is rare in humans below age 45, rises rapidly to age 65, and remains high thereafter. The median life span of patients with chronic myelogenous leukemia from the time of diagnosis is approximately four years.

Patients with chronic CML have usually been treated with alkylating agents such as busulfan or by treatment with hydroxyurea. In recent years treatment with $\alpha$-interferon has been used.

These therapeutic agents can have serious side effects. For example, busulfan can cause a serious complication known as "busulfan lung" that leads to broncho-pulmonary dysplasia with pulmonary fibrosis. Although these therapeutic agents improve the quality of life, there is little evidence to suggest that these agents improve the life span of these patients. Ultimately, most patients develop the accelerated blast crisis phase of the disorder that is generally much less susceptible to treatment.

About 60 to 80 percent of patients with CML develop a blast crisis. This blast crisis represents a manifestation of acute leukemia. The presence of certain markers on the blast cells sometimes suggests a lymphold origin of these cells during the blast crisis.

Chemotherapeutic agents used for the treatment of the blast crisis are the same as those used for the treatment of other acute leukemias. For example, cytarabine and daunorubicin, used for the treatment of acute myelocytic leukemia, is used to treat CML blast crisis. Prednisone and vincristine, a therapeutic regime used in the treatment of acute lymphocytic leukemias, is also used to treat CML blast crisis. Nevertheless, these drug therapies of the blast crisis stage of CML are even less successful than are the treatments of other acute leukemias.

Cytologically, CML is characterized by a translocation between chromosome 22 and chromosome 9. This translocation juxtaposes a proto-oncogene with tyrosine kinase activity, a circumstance that apparently leads to uncontrolled cell growth. The resulting translocated chromosome is sometimes referred to as the Philadelphia chromosome.

Although busulfan and hydroxyurea can be effective in treating chronic myelogenous leukemia, the bone marrow of treated patients still contains a predominance of cells with the translocation. In contrast, the marrow of patients treated with $\alpha$-interferon sometimes loses the clone with the translocation. This result suggests that $\alpha$-interferon may alter the natural course of the disease. There is, as yet, no evidence that this is the case.

2-Chlorodeoxyadenosine (2-CdA) is a deoxyadenosine analog that is resistant to adenosine deaminase. This drug is used extensively in the treatment of patients with lymphoid neoplasms and with autoimmune hemolytic anemia. Piro et al., *Blood* 72:1069–1073 (1988); Carson, In: *Purine and Pyrimidine Metabolism in Man*, Plenum Publishing Corp., New York, pp. 427–431, 1989; Piro et al. *Blood* 72 (Suppl 1):220A, (1988) (Abstract); Saven et al., *Blood* 74:239A (1989); Kay et al. *Blood* 74:121A (1989); Piro et al., *N. Engl. J. Med.* 322:1117–1121 (1990); Carson et al., *Proc. Natl. Acad. Sci. USA*, 81:2232–2236 (1984). 2-CdA has also been used in the treatment of certain autoimmune diseases, particularly rheumatoid arthritis.

These disorders are all related in that the involved cells are lymphocytic or monocytic in origin. For example, hairy cell leukemia, against which 2-CdA is the treatment of choice, is a disease of B-lymphocytes. Rheumatoid arthritis, a disease of uncertain etiology, is known to involve both lymphocytes and monocytes.

2-CdA has also been used in the treatment of CML in blast crisis. In a Phase I trial of two patients, 2-CdA treatment led to a decrease in blast count in one patient, and a loss of detectable tumor in another patient. Carson et al., *Proc. Natl. Acad. Sci. USA*, 81:2232–2236 (1984). However, patients not in blast crisis; i.e., those suffering from the chronic phase of CML, were not examined in this study. As discussed elsewhere, the blast crisis of CML is characterized by the proliferation of cells of lymphoid origin and is an acute leukemia that has heretofore been thought to require a different type of treatment than does the chronic form of this leukemia.

Clinical and in vitro studies have therefore focussed primarily on the use of 2-CdA on diseases with lymphocytic or monocytic involvement.

The effect of 2-CdA on in vitro on cultured marrow and blood cells from normal patients has been reported [Petzer et al., *Blood*, 78:2583-2587 (1991)] in a study published after the work underlying this invention was well underway. Erythroid progenitor cells showed a dose-dependent sensitivity to 2-CdA, with that sensitivity decreasing as the stage of progenitor maturation .increased. Primitive burst-forming unit-erythroid (pBFU-E) cells displayed an $IC_{50}$ value (i.e., the concentration required to inhibit 50 percent of growth) of 19 nanomoles (nmol) per liter (nM). Mature BFU-E (mBFU-E) cells displayed $IC_{50}$ values of 38 nM. The last progenitor cell in the erythroid pathway, colony forming unit-erythroid (CFU-E) cells, displayed $IC_{50}$ values of 56 nM. Colony forming unit-granulocyte macrophage (CFU-GM) cells, progenitor cells to granulocytes (including neutrophils, eosinophils and basophils) and macrophages, displayed an $IC_{50}$ value of 16 nM in that study.

In a conflicting report, growth of CFU-GM cells was enhanced by 23 percent to 35 percent when exposed to 1 nM or 10 nM 2-CdA. A reduction of 60 percent was noted at a 2-CdA concentration of 100 nM. Carson et al. *Blood*, 62:737-743, 1983.

Results obtained in clinical trials of 2-CdA on various diseases also conflict with regard to the effects of the drug on neutrophils. For example, treatment of chronic lymphocytic leukemia at serum levels less than 10 nM led, in most cases, to an increase in neutrophil count. Piro et al., *Blood*, 72:1069-1073 (1988). 2-CdA administered at 0.1 mg/kg per day over a 7 day period to patients with cutaneous T cell lymphoma showed that the neutrophils in these patients were more resistant to 2-CdA than their monocytes and lymphocytes. Carrera et al., *J. Clin. Invest.*, 86:1480-1488 (1990).

However, treatment of hairy cell leukemia led to transient neutropenia, with granulocyte counts under 500 per microliter. This effect was particularly acute in patients who were already neutropenic. Beutler et al., *Leuk. Lymphoma*, 5:8 (1991).

Still further, in previously unreported results relating to treatment of patients with multiple sclerosis, granulocyte counts were substantially unchanged after several courses of treatments with 2-CdA at about 0.1 mg/kg/day over seven day treatment courses of continuous infusion. Those results are illustrated and discussed hereinafter in Example 3.

SUMMARY OF THE INVENTION

The present invention contemplates a process for treating chronic myelogenous leukemia. The compound utilized in the present invention as the active ingredient is a 2-halo-2'-deoxyadenosine.

The process for treating chronic myelogenous leukemia comprises administering to a host mammal having chronic myelogenous leukemia a therapeutically effective amount of a substituted adenosine derivative dissolved or dispersed in a pharmacologically acceptable carrier or diluent. That adenosine derivative has a structure that corresponds to that of Formula I:

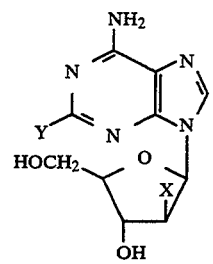

wherein Y is halogen, and X is hydrogen or fluoro. Y is preferably chloro.

A sufficient amount of one, or more, of the above compounds of Formula I, dissolved or dispersed in a pharmacologically acceptable carrier or diluent is used, to provide a therapeutically effective amount.

Depending upon the treatment modality, the administration of a compound of Formula I is typically carried out by providing about 0.04 to about 1.0 milligrams per kilogram of body weight, or more preferably by providing about 0.05 to about 0.20 mg/kg body weight per day. That treatment modality is typically repeated over a five to seven day course.

In administering the treatment of the present invention, granulocytes of a host mammal with CML (neoplastic granulocyte precursors) are contacted with a composition containing a pharmacologically acceptable carrier that itself contains dissolved or dispersed therein a substituted adenosine derivative having a structure that corresponds to that of Formula I as an active ingredient or agent. The neoplastic granulocyte precursors are contacted in vivo by administration of the composition to a mammal such as a human.

Also contemplated is a preferred process for treating chronic myelogenous leukemia that comprises administering to a human having chronic myelogenous leukemia an amount of about 0.04 to about 1.0 milligrams per kilogram of body weight of a substituted adenosine derivative as an active ingredient dissolved or dispersed in a pharmacologically acceptable carrier or diluent. That adenosine derivative has a structure that is represented by Formula II:

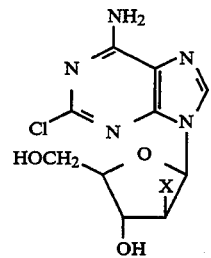

wherein X is hydrogen or fluoro.

A most preferred compound useful herein as active ingredient is 2-chloro-2'-deoxyadenosine (2-CdA) whose structure is shown below.

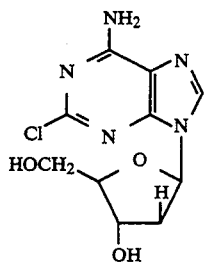

2-CdA

Particularly preferred compounds of Formula II contain a fluoro group at the 2'-position. Most preferred is 2-chloro-2'-deoxy-2'-arafluoroadenosine (2-CdAF), whose structure is shown below.

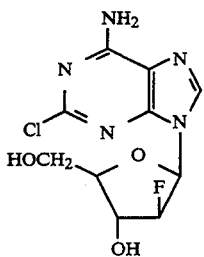

2-CdAF

The process of treatment contemplated in this invention decreases the level of neoplastic granulocyte precursors in the blood as a result of the specific cytotoxicity of the compounds utilized toward neoplastic granulocyte precursors.

The present invention has several benefits and advantages.

A major advantage of the invention is that it provides a new, effective treatment for the chronic phase of CML.

Another advantage of the invention is that its use avoids many of the potentially severe side effects of current drug therapies.

Yet another advantage of the invention is that its processes can be practiced by both parenteral and oral administration.

Still further benefits and advantages of the invention will be apparent to those skilled in the art from the description that follows.

DETAILED DESCRIPTION OF THE INVENTION

The present invention contemplates a process for treating chronic myelogenous leukemia. It is to be understood that the neutropenia and reduction of neoplastic granulocyte numbers discussed hereinafter using a process of the invention were quite unexpected, given the conflicting data from both in vitro and in vivo studies on 2-CdA, discussed elsewhere.

In a contemplated process, a therapeutically effective amount of a substituted adenosine derivative (2-halo-2'-deoxyadenosine) as an active ingredient dissolved or dispersed in a pharmaceutically acceptable carrier or diluent is administered to a host mammal having CML. That substituted adenosine derivative has a structure that corresponds to that of Formula I:

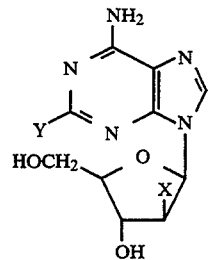

I wherein Y is halogen, and X is either hydrogen or fluoro.

In a preferred embodiment, Y is chloro.

Also contemplated is a process for treating chronic myelogenous leukemia that comprises administering to a human having chronic myelogenous leukemia an amount of about 0.04 to about 1.0 milligrams per kilogram of body weight of a substituted adenosine derivative as an active ingredient dissolved or dispersed in a pharmacologically acceptable carrier. That adenosine derivative has a structure that is represented by Formula II:

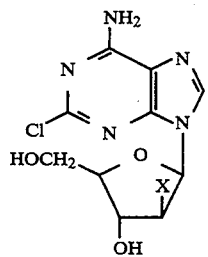

II wherein X is hydrogen or fluoro.

The substituted adenosine derivative is present in the composition in an amount sufficient to provide a therapeutically effective amount (dose) over the period of contacting.

It is noted that when X is hydrogen the sugar ring can be named as a 2'-deoxyribosyl or 2'-deoxyarabinofuranosyl radical. Both nomenclatures are utilized herein. When the class of compounds embraced by Formula I or Formula II is discussed, all of the compounds are considered herein as derivatives of ribose and are therefore named as adenosine or deoxyadenosine derivatives. However, when specific compounds of the subclass where X=F are discussed, the prefix "ara" is used, as in 2-chloro-2'-deoxy-2'-arafluoroadenosine. All of these compounds are also referred to herein more simply as an adenosine derivative.

In the above formulas, and in all other formulas shown herein, hydrogen atoms on the purine and furanosidyl rings that are not needed to show conformation about a particular bond are not shown. Thus, the 7-position adenine hydrogen is not shown.

Of the compounds of Formula II, those where X is fluoro are particularly preferred for use by oral administration.

It is to be noted that the designation "halogen" used herein is meant to include fluorine, chlorine and bromine derivatives, and to exclude iodine derivatives, which are unstable and decompose, and astatine derivatives that are radioactive. Where specific halogen derivatives are intended, those compounds are named specifically.

A compound of Formula I dissolved or dispersed in or together with a pharmacologically acceptable carrier or diluent constitutes a composition useful in this invention. However, since a compound of Formula II is embraced by Formula I, and a composition containing a compound of Formula II is useful in a process of the invention, a composition containing a compound of Formula II will frequently be discussed hereinafter in terms of a composition of a compound of Formula I. Such a composition is useful in carrying out the treatment method of the invention.

A compound of Formula I is useful in both short and long term treatment. For instance, a 2-halo-9,1'-beta-2'-deoxy-2'-fluoro-D-arabinofuranosyladenine is administered to the warm-blooded animal internally, e.g., parenterally, orally, or rectally as a suppository, in an effective amount.

Although a compound of Formula I can be administered as the pure chemical, it is preferred that it be administered as a pharmaceutical composition. In either event, it is administered in an amount sufficient to provide a therapeutically effective amount as is discussed hereinafter.

Accordingly, the present invention utilizes a pharmaceutical composition comprising a therapeutically effective amount of a compound of Formula I or Formula II, preferably wherein X is hydrogen, hereinafter referred to as the "active ingredient" or "agent," dissolved or dispersed in a pharmacologically acceptable carrier or diluent.

A pharmaceutical composition is prepared by any of the processes well known in the art of pharmacy all of which involve bringing into association the active compound and the carrier therefor. For therapeutic use, a compound utilized in the present invention can be administered in the form of conventional pharmaceutical compositions. Such compositions can be formulated so as to be suitable for oral or parenteral administration, or as suppositories. In these compositions, the agent is typically dissolved or dispersed in a physiologically tolerable carrier.

A carrier or diluent is a material useful for administering the active compound and must be "pharmacologically acceptable" in the sense of being compatible with the other ingredients of the composition and not deleterious to the recipient thereof. Thus, as used herein, the phrases "physiologically tolerable" and "pharmacologically acceptable" are used interchangeably and refer to molecular entities and compositions that do not produce an allergic or similar untoward reaction, such as gastric upset, dizziness and the like, when administered to a mammal such as a laboratory animal or human. The physiologically tolerable carrier can take a wide variety of forms depending upon the preparation desired for administration and the intended route of administration.

As an example of a useful composition, a compound of Formula I can be utilized in liquid compositions such as sterile suspensions or solutions, or as isotonic preparations containing suitable preservatives. Particularly well-suited for the present purposes are injectable media constituted by aqueous injectable isotonic and sterile saline or glucose solutions. Additional liquid forms in which these compounds can be incorporated for administration include flavored emulsions with edible oils such as cottonseed oil, sesame oil, coconut oil, peanut oil, and the like, as well as elixirs and similar pharmaceutical vehicles;. One or more pharmaceutically acceptable preservatives can also be present in a composition.

In one preferred mode of administration, a liquid composition is administered by intravenous infusion. This is illustrated in Example 1, hereinafter.

In another mode of administration, a liquid composition is administered subcutaneously or intramuscularly. Such a composition is substantially identical in composition to a composition used for intravenous infusion.

The active agent can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

An agent of Formula I can also be used in compositions such as tablets or pills, preferably containing a unit dose of the compound. To this end, the agent (active ingredient) is mixed with conventional tableting ingredients such as corn starch, lactose, sucrose, sorbitol, talc, stearic acid, magnesium stearate, dicalcium phosphate, gums, or similar materials as non-toxic, physiologically tolerable carriers. The tablets or pills can be laminated or otherwise compounded to provide unit dosage forms affording prolonged or delayed action.

It should be understood that in addition to the aforementioned carrier ingredients the pharmaceutical formulation described herein can include, as appropriate, one or more additional carrier ingredients such as diluents, buffers, flavoring agents, binders, surface active agents, thickeners, lubricants, preservatives (including antioxidants) and the like, and substances included for the purpose of rendering the formulation isotonic with the blood of the intended recipient.

The tablets or pills can also be provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate phthalate, and the like. A particularly suitable enteric coating comprises a styrene-maleic acid copolymer together with known materials that contribute to the enteric properties of the coating. Methods for producing enteric coated tablets are described in U.S. Pat. No. 4,079,125 to Sipos, which is herein incorporated by reference.

The term "unit dose," as used herein, refers to physically discrete units suitable as unitary dosages for administration to warm blooded animals, each such unit containing a predetermined quantity of the agent calculated to produce the desired therapeutic effect in association with the pharmaceutically acceptable diluent. Examples of suitable unit dosage forms in accord with this invention are tablets, capsules, pills, powder packets, granules, wafers, cachets, teaspoonfuls, dropperfuls, ampules, vials, segregated multiples of any of the foregoing, and the like.

Oral administration of the compound is a particularly attractive mode of administration. One drawback usually associated with oral administrations of bioactive nucleoside compounds, however, is their potential decomposition in the acidic conditions of the stomach. That is, the glycosidic bond tends to hydrolyze under acid conditions.

However, where oral administration is desired, substitutions on the 2-position of the adenine ring of the compound of Formula I are preferably utilized along with a 2'-fluoro-substituted arabinofuranosidyl ring. The before-discussed enteric coating for a capsule or pill containing a compound of Formula I where X is hydrogen (H) can also be used for oral administration. Alternatively, the co-administration of a drug that neutralizes gastric activity or prevents the secretion of acid by the stomach such as cimetidine hydrochloride can also be utilized in lieu of an enteric coating.

Marquez et al., Biochem. Pharm., 36:2719–2722 (1987) reported preparation of 2'-fluoro-2',3'-dideoxyribose and 2'-fluoro-2',3'-dideoxyarabinose derivatives of adenosine. Their findings stated that both derivatives were stable at a pH value of 1 at 37 degrees C., whereas dideoxyadenosine had a half-time of 35 seconds under those conditions.

The synthesis and use of 2-halo-2'-deoxy-2'-arafluoroadenosine derivatives is also disclosed in U.S. Pat. No. 5,034,518, No. 4,918,179 and No. 4,751,221, whose disclosures are incorporated herein by reference.

It is particularly contemplated that the administering of a contemplated substituted adenosine derivative involve contact between the neoplastic granulocyte precursors and that adenosine derivative in vivo. Thus, a composition containing a compound of Formula I is administered in vivo to a mammal affected with such a disorder in amounts sufficient to provide a therapeutically effective amount of each drug to the mammal. The composition is maintained within the mammal host until its constituent components are eliminated by usual bodily processes.

The amount of a compound of Formula I present in a composition and used in a process as described above is a function of several variables, as is well known in the medicinal arts. Among those variables are the mammal treated, and the process of administration. Exemplary concentrations are illustrated hereinafter.

The amount administered is less than that which substantially impairs bone marrow functions as determined by usual procedures, and is sufficient to provide a normal granulocyte count, or a less than normal count, in the treated host mammal. The above amount of a 2-halo-2'-deoxyadenosine derivative of Formula I in the composition is also an amount sufficient to provide about 0.04 to about 1.0 mg/kg of body weight of the treated host mammal per day, more preferably about 0.05 to about 0.20 mg/kg/day, and most preferably about 0.1 mg/kg/day, when given in vivo by intravenous infusion, intramuscularly or subcutaneously. Oral administration typically utilizes about twice the amount of a 2-halo-2'-deoxyadenosine derivative. These amounts are another way of defining a therapeutically effective amount that is particularly useful when a compound of Formula I is administered by infusion.

Preliminary studies show that 2-CdA and CAFdA exhibit similar in vitro and in vivo activities. Those in vitro studies (Example 4, hereinafter) indicate that 2-CdA is about 2 to 3 times more active per unit weight than is CAFdA. As a consequence, for parenteral administration, CAFdA is given at about 2 to about 3 times the dose of 2-CdA. Further, preliminary in vivo studies (Example 5) show that 2-CdA is ineffective when given orally without the protection of an enteric coating, whereas CAFdA is effective when administered per orally.

The molar plasma concentration of the compound of Formula I during treatment is preferably in the range of about 1 nanomolar (nM) to about 100 nM, particularly about 5 nM to about 50 nM, and more preferably about 10 nM to about 20 nM. Molarity of the 2-halo-2'-deoxyadenosine derivative in plasma of the treated (administered to) animal thus provides still another measure of a therapeutically effective dose from which the amount in a composition can be calculated.

It is to be understood that the above therapeutically effective dosages need not be the result of a single administration, and are usually the result of the administration of a plurality of unit doses. Those unit doses can in turn comprise portions of a daily or weekly dosage, and thus, the therapeutically effective dose is determined over the period of treatment (contacting).

Oral administration is the preferred mode of administration for the 2-halo-2'-arafluoroadenosine derivatives, as already noted. To achieve the desired plasma concentration of the agent, a range of doses can be employed depending upon the specific mode of administration, objective of the particular treatment, the particular compound being used, and like considerations.

For example, for oral administration, the daily dose can be about 0.04 to about 1.0 mg/kg of body weight, more preferably about 0.05 to about 0.20 mg/kg of body weight, and most preferably about 0.1 mg/kg of body weight. In general, the amount of active substituted adenosine derivative administered can vary over a relatively wide range to achieve, and preferably maintain, the desired plasma concentration.

Unit dosage forms of the adenosine derivative can contain about 0.1 milligrams to about 15 milligrams thereof. A preferred unit dosage form contains about 0.1 to about 1 milligram of agent and can be administered 2 to 5 times per day. However, it should be noted that continuous infusion at a rate designed to maintain the above described plasma concentration is also contemplated. That continuous infusion is typically carried out over a 5–7 day time period.

Duration of a particular treatment can also vary, depending on severity of the disease, and the hematological response obtained. Typical administration lasts for a time period of about 5 to about 14 days, with a 7-day time course being usual. Courses (cycles) of administration can also be repeated at monthly intervals, or parenteral unit dosages can be delivered at weekly intervals. Oral unit dosages can be administered at intervals of one to several days to provide the determined therapeutically effective dose. Thus, administration of a before-discussed dosage over a time period of about 5 to about 14 days or at weekly or daily intervals provides an amount sufficient to kill at least about 50 percent of the originally present neoplastic granulocyte precursors.

This process of treatment produces a decrease in the level of total granulocytes and thus neoplastic granulocyte precursors in the blood due to the toxicity of the utilized compounds of Formula I toward neoplastic granulocyte precursors. This process can be used to reduce the number of total granulocytes circulating in a treated mammal's blood stream by greater than 95 percent and in some cases greater than 99 percent of the number present prior to treatment over the treatment period, and provide a treated host mammal with a "normal" or a lower than normal granulocyte count. Humans are typically treated until their total granulocyte counts are about 10 percent of a normal count.

Indeed, this process can induce complete hematological remission in patients suffering from CML. It is preferred to treat a host mammal to obtain complete hemotological remission as normally assayed to provide normalization of peripheral leukocyte counts, platelet counts and resolution of splenomegaly that normally accompany the greatly enhanced granulocyte counts exhibited with this disease state.

Exemplary studies are illustrated hereinafter.

EXAMPLES

The present invention is further illustrated by the following examples which are not intended to limit the scope of the invention in any way.

Example 1: Hematological Remission in Patients with CML

2-CdA was administered to 5 patients with stable phase CML, previously maintained on hydroxyurea and/or α-interferon, at a course of 0.1 mg/kg per day by continuous intravenous infusion for 7 days. The 2-CdA was dissolved in 0.9 percent aqueous saline containing an additional 0.1 percent benzyl alcohol as preservative. Each course was repeated every 28 days until the maximum hematological remission response of the treatment was achieved. The median age of the patients was 60 years, with a range of 52 to 75 years. There were 3 males and 2 females. A median of 2 courses of treatment was administered, with a range of 1 to 4 courses. All five patients obtained complete hematological remissions as defined by normalization of peripheral leukocyte counts, platelet counts, and resolution of splenomegaly.

Patient 1 had been treated with hydroxyurea prior to 4 courses of 2-CdA treatment. Upon follow-up 5.7 months later, this patient showed complete hematological remission.

Patient 2 had also been treated with hydroxyurea prior to 2 courses of 2-CdA treatment. Upon follow-up 3.0 months later, this patient showed complete hematological remission.

Patient 3 had been treated with a combination of hydroxyurea and α-interferon prior to 3 courses of 2-CdA treatment. Upon follow-up 3.2 months later, this patient showed complete hematological remission.

Patient 4 had also been treated with a combination of hydroxyurea and α-interferon prior to 1 course of 2-CdA treatment. Upon follow-up 1.5 months later, this patient showed complete hematological remission.

Patient 5 had been treated with hydroxyurea prior to 2 courses of 2-CdA treatment. Upon follow-up 1.0 months later, this patient showed complete hematological remission.

The median follow-up was 3.2 months, with a range from 1.0 to 5.7 months. All patients continue to be in hematologic remission, but have persistence of the Philadelphia chromosome. No toxicity attributable to 2-CdA was encountered.

Example 2: Effects of 2-CdA on Granulocytes in a Patient with CML

The effect of 2-CdA administration upon the level of total circulating peripheral blood granulocytes was determined on a patient with CML following the second and third courses of therapy as discussed in Example 1.

During the second course of 2-CdA therapy, the patient began the therapy on treatment day zero with a granulocyte count of $34,831/\mu l$. By day 5, the granulocyte count had dropped to $27,724/\mu l$. By day 13, the granulocyte count had dropped to $210/\mu l$, a decrease from the granulocyte count at day zero in excess of 99 percent. By day 17, the granulocyte count was at $690/\mu l$, representing a decrease of over 98 percent relative to the granulocyte count at day zero. (Granulocyte counts are given per microliter and those units are to be inferred hereinafter where a unitless number is provided.

During the third course of 2-CdA therapy, the granulocyte count on day zero was 11,060. By day 5, the granulocyte count had decreased to 5,676. By day 14, the granulocyte count had decreased to a level of 270, representing an approximately 98 percent decrease from the initial granulocyte level. By day 17, the granulocyte count was 525, a level 95 percent lower than the initial granulocyte count.

Example 3: Effects of 2-CdA on Two Non-CML Patients

Granulocyte counts were obtained from two patients who were receiving 2-CdA in the treatment of a non-leukemic disease, multiple sclerosis. These patients therefore had normal granulocytes. Table 1 below shows that 2-CdA treatment of these patients did not affect the granulocyte count.

TABLE 1

| Day of 2-CdA Treatment | Granulocyte Counts* Patient | | | | |
|---|---|---|---|---|---|
| | R.P.[1] | R.P.[2] | R.H.[1] | R.H.[3] | R.H.[4] |
| 1 | 4.14 | 3.14 | 6.69 | 4.56 | 3.18 |
| 3 | 3.91 | 3.02 | 5.35 | 4.12 | 4.89 |
| 5 | 4.83 | 3.27 | 4.75 | 4.39 | 4.27 |
| 7 | 6.06 | 3.30 | 4.89 | 3.56 | 3.69 |
| 14 | 4.21 | 2.43 | 3.23 | 3.64 | 2.22 |

*Cells $\times 10^{-3}/\mu l$
[1]At first cycle of treatment
[2]At sixth cycle of treatment
[3]At fourth cycle of treatment
[4]At fifth cycle of treatment Example 4: In Vitro Cytotoxicities of 2-CdA and CAFdA Toward Selected Cell Lines are Similar Seven different cell lines were treated with varying concentrations of 2-chloro-9,1'-beta-2'-deoxy-2'-fluoro-D-arabinofuranosyladenine (CAFdA) to determine percent viability. CAFdA concentrations ranging from 0 to about 260 nM were used to treat each cell line in vitro.

A B cell line, denoted SB, was least sensitive to the compound, with 90 percent viability when treated with about 260 nM CAFdA. A myeloid cell line, designated K562, was more sensitive than the SB cell line, with 40 percent viability at about 260 nM CAFdA.

Of the other five cell lines, two were T cell lines, one called CEM and the other Molt-4, and the remaining three were monocyte-like cell lines, designated THP-1, U937 and HL-60, respectively. These five cell lines all exhibited substantial sensitivity, with all five showing less than 20 percent viability at about 60 nM CAFdA, and less than 10 percent viability at concentrations above about 130 nM CAFdA. At dosages between about 25 and about 50 nM CAFdA, two monocyte-like cell lines, THP-1 and HL-60, and one of the T cell lines, CEM, displayed a greater sensitivity, with about 60 percent or less viability, than the other cell lines tested. Similar results were found for 2-CdA in a companion study using some of the same and some different cell lines.

The two compounds, 2-CdA and CAFdA, were also compared for invitro activity against another group of human cell lines in a direct comparative assay. The results of that study are shown below in Table 2.

TABLE 2

| Cell Type[2] | $ID_{50}$ (nM)[1] | | |
|---|---|---|---|
| | CdA | CAFdA | CAFdA/2-CdA |
| CEM, wild type | 21 | 67 | 3.1 |
| CEM, deoxyeytidine kinase deficient | 716,000 | 716,000 | — |
| CEM, Increased 5'-nucleoside | 60 | 126 | 2.1 |
| DHL9, wild type | 80 | 150 | 1.9 |
| DHL9, Increased ribonucleotide reduction | 4,000 | 6,000 | 15. |
| Peripheral blood lymphocytes | 15 | 18 | 1.9 |
| Monocytes | 22 | 47 | 2.1 |

[1]Concentration that produced 50 percent reduction in all numbers after five days
[2]CEM cells are T lymphoblasts; DHL9 cells are lymphoblasts.

The results of these two studies indicate a similar toxicity profile for the two compounds, with 2-CdA being of similar to slightly greater potency as compared to CAFdA.

Example 5: Oral and IP Effects of 2-CdA and CAFdA on Delayed-Type Hypersensitivity Delayed-type hypersensitivity (DTH) is a cell-mediated immune response that typically takes longer than 12 hours to develop. In the guinea pig, a DTH reaction to an antigen can be established by first immunizing the animal with the antigen in an adjuvant such as Freund's complete adjuvant. Subsequent intradermal injection of the antigen causes no change for at least 10 hours, after which there is a gradual increase in erythema and swelling in response to antigen injection. This response peaks about at about 24 hours after challenge, then gradually subsides.

Histologically, the inflammatory response is characterized by intense inundation of the site with mononuclear cells, of which about half are lymphocytes and the other half monocytes. DTH is therefore an indicator of a monocyte-mediated immune reaction.

In one study, guinea pigs were sensitized to ovalbumin in adjuvant. The animals were then treated either orally or intraperitoneally with saline (control), dexamethasone (5 mg/kg), 2-CdA E1 mg/kg) or CAFdA (1 mg/kg). The animals were then injected with ovalbumin intradermally to elicit the DTH response. The mean area of the swelling size was measured for each animal (nine or ten animals were treated for each protocol).

Both dexamethasone and CAFdA, regardless of the route of administration, showed a significant inhibition of swelling at both 24 and 48 hours after ovalbumin challenge compared to control saline treated animals (p <0.01 by Student's t-test). 2-CdA, on the other hand, was ineffective when given by the oral route, indicating the desirability of use of an enteric coating for oral administration, but caused significant inhibition of swelling compared to control animals when given intraperitoneally (p <0.01 by Student's t-test).

In another study, the effects of different dosages of 2-CdA on the DTH reaction were examined. Guinea pigs sensitized to ovalbumin were treated with saline (control), dexamethasone (5 mg/kg), and 2-CdA at 1 mg/kg or 0.1 mg/kg. Three days after treatment, the animals were challenged with ovalbumin intradermally. The areas of the skin lesions were measured at 6, 24, and 48 hours after challenge.

All three doses of therapeutic agents were effective at inhibiting swelling at 24 and 48 hours post-challenge when compared to control saline treated animals (p <0.01 by Student's t-test). The numerical values of the areas of swelling were lower in the 2-CdA treated animals at both dosages when compared to dexamethasone-treated animals. The numerical values for 0.1 and 1.0 mg/kg 2-CdA were substantially the same, and were slightly less than the value obtained with dexamethasone.

| Ingredient | Amount. mg/Tablet |
|---|---|
| Example 6: Compressed Tablet | |
| 2-Chloro-9,1'-beta-2'-deoxy-2'-fluoro-D-arabinofuranosyladenine | 1 |
| Dibasic Calcium Phosphate NF | q.s |
| Starch USP | 40 |
| Modified Starch | 10 |
| Magnesium Stearate USP | 1–5 |

| Ingredient | Amount. mg/Capsule |
|---|---|
| Example 7: Hard Shell Capsule | |
| 2-Bromo-9',1'-beta-2'-deoxy-2'-fluoro-D-arabinofuranosyladenine | 1 |
| Lactose, Spray Dried | q.s |
| Magnesium Stearate USP | 1–10 |

| Ingredient | Amount. % wt./vol. |
|---|---|
| Example 8: Oral Liquid (Syrup) | |
| 2-Fluoro-9,1'-beta-2'-deoxy-2'-fluoro-D-arabinofuranosyladenine | 0.5 |
| Liquid Sugar | 75.0 |
| Methyl Paraben USP | 0.18 |
| Propyl Paraben USP | 0.02 |
| Flavoring Agent | q.s. |
| Purified Water, q.s. ad | 100.0 |

| Ingredient | Amount. % wt./vol. |
|---|---|
| Example 9: I.V. Injectable Solution Concentrate | |
| 2-Chloro-9,1'-beta-2'-deoxy-adenosine | 0.1 |
| Benzyl Alcohol NF | 0.9 |
| Purified Water | 100.0 |

Example 10: Enteric Coated Adenine Derivative

Table 3 lists the components of a drug composition used in the present invention (Composition A) and an enteric coating composition (Composition B).

TABLE 3

| Ingredient | Weight |
|---|---|
| Composition A | |
| 2-Chloro-9,1'-beta-2'-deoxyadenosine | 67.0 |
| Polyvinylpyrrolidone | 1.3 |

TABLE 3-continued

| Ingredient | Weight |
| --- | --- |
| Modified Starch | 5.0 |
| Sodium Bicarbonate (anhydrous) | 20.0 |
| Citric Acid | 6.7 |
|  | 100.0 |
| Composition B | |
| Chloroform | 66.4 |
| Methanol (anhydrous) | 15.4 |
| Cellulose Acetate Phthalate | 7.2 |
| Talc #127 U.S.P. | 7.3 |
| FD & C #5 Yellow | 1.0 |
| Diethyl Phthalate | 2.7 |
|  | 100.0 |

The ingredients listed for Composition A are mixed, together with the slow addition of anhydrous isopropyl alcohol (700 ml per kg of Composition A) for about 9 to 15 minutes, The resulting blend is then segmented into tablets by extrusion. These segmented particles are dried in an oven at 35 degrees C. for about 40 to about 48 hours. The dried granules are sized through a 14 mesh screen. Those segments that pass through the screen are compressed in a tablet machine to produce tablets about 4.8 mm in diameter and about 4 mm thick.

The dried tablets are then coated with the pH sensitive enteric coating composition (Composition B) in a pan employing about 0.45 liters of Composition B per kilogram of tablets to give a uniform coating weighing about 5.5% by weight of the final tablet. The wet coated tablets are then dried.

The foregoing description and the examples are intended as illustrative and are not to be taken as limiting. Still other variations within the spirit and scope of this invention are possible and will readily present themselves to those skilled in the art.

What is claimed is:

1. A process for treating chronic myelogenous leukemia that comprises administering to a host mammal having chronic myelogenous leukemia a therapeutically effective amount of a substituted adenosine derivative as an active ingredient dissolved or dispersed in a pharmacologically acceptable carrier, said adenosine derivative having a structure represented by the formula:

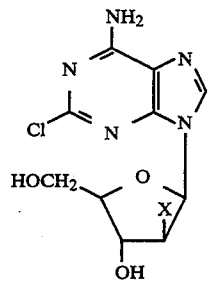

wherein Y is halogen, and X is hydrogen.

2. The process of claim 1 wherein Y is chlorine.

3. The process of claim 1 wherein said administering provides said adenosine derivative in the plasma of said host mammal in an amount of about 0.04 to about 1.0 milligrams per kilogram of host mammal body weight per day.

4. The process of claim 1 wherein said adenosine derivative is administered parenterally.

5. The process of claim 1 wherein said host mammal is a human.

6. A process for treating chronic myelogenous leukemia that comprises administering to a human having chronic myelogenous leukemia an amount of about 0.04 to about 1.0 milligrams per kilogram of body weight of a substituted adenosine derivative as an active ingredient dissolved or dispersed in a pharmacologically acceptable carrier, said adenosine derivative having a structure represented by the formula:

wherein X is hydrogen or fluoro.

7. The process of claim 6 wherein said administering provides said adenosine derivative in the plasma of said host mammal in an amount of about 0.05 to about 0.20 milligrams per kilogram of host mammal body weight per day.

8. The process of claim 7 wherein said adenosine derivative is administered parenterally.

* * * * *